United States Patent [19]

Finkenzeller et al.

[11] 4,019,061
[45] Apr. 19, 1977

[54] X-RAY EXAMINING APPARATUS FOR EXAMINATION OF STANDING PATIENTS

[75] Inventors: Johann Finkenzeller, Erlangen-Tennenlohe; Fritz Bronnert; Karl Weiss, both of Erlangen, all of Germany

[73] Assignee: Siemens Aktiengesellschaft, Berlin & Munich, Germany

[22] Filed: May 20, 1976

[21] Appl. No.: 688,724

Related U.S. Application Data

[63] Continuation-in-part of Ser. No. 501,071, Aug. 27, 1974, abandoned.

[30] Foreign Application Priority Data

Sept. 12, 1973 Germany ............................ 2346024

[52] U.S. Cl. ................................ 250/470; 250/468
[51] Int. Cl.² ............................................. G11B 1/00
[58] Field of Search ............ 250/468, 469, 470, 475

[56] References Cited

UNITED STATES PATENTS

| | | | |
|---|---|---|---|
| 2,795,702 | 6/1957 | Morris | 250/470 |
| 3,448,979 | 6/1969 | Farmer | 250/470 |
| 3,855,476 | 12/1974 | Farmer | 250/470 |

*Primary Examiner*—Alfred E. Smith
*Assistant Examiner*—Bruce C. Anderson
*Attorney, Agent, or Firm*—Hill, Gross, Simpson, Van Santen, Steadman, Chiara & Simpson

[57] ABSTRACT

An X-ray examining apparatus for the examination of upstanding patients, including an X-ray tube which is suspended from a support, and an exposure installation vertically adjustably mounted on a rack incorporating conveying means for the conveyance of film sheets from a supply magazine into an exposure position and from the exposure position into an automatic developing arrangement.

7 Claims, 2 Drawing Figures

X-RAY EXAMINING APPARATUS FOR EXAMINATION OF STANDING PATIENTS

The present application is a continuation-in-part of the parent application Ser. No. 501,071 filed Aug. 27, 1974 now abandoned.

FIELD OF THE INVENTION

The present invention relates to an X-ray examining apparatus for the examination of upstanding patients, including an X-ray tube which is suspended from a support, and an exposure installation vertically adjustably mounted on a rack incorporating conveying means for the conveyance of film sheets from a supply magazine into an exposure position and from the exposure position into an automatic developing arrangement.

DISCUSSION OF THE PRIOR ART

In recent times, in X-ray examining apparatus in which there has been observed a reduction in cassette operation and greater application of film magazine techniques, it has been found necessary that the magazines containing the X-ray films be protected from the X-radiation and scattered X-radiation. In this connection, there has become known an X-ray targeting apparatus having film sheet magazines, which includes a film carriage movable from a ray-protected stand-by position into a film exposure position and back again, at least one magazine cassette for the unexposed and exposed films, as well as conveying means for carrying out the loading and unloading of the film carriage in the stand-by position, and wherein the magazine cassettes, as well as the conveying means located between the loading and unloading sides of the film carriage and the therewith associated magazine cassettes, are located in the ray-protected region of the stand-by position of the film carriage. In this construction of the X-ray targeting apparatus, the width thereof which must be considered is approximately 3½ times the maximum exposure width, has been found to be disadvantageous.

SUMMARY OF THE INVENTION

Accordingly, it is an object of the present invention to provide an X-ray examining apparatus including a supply magazine for sheet films which has been considerably reduced spatial requirements.

In an X-ray examining apparatus of the above-mentioned type, the supply magazine for the unexposed film sheets inventively is located, in the direction of the incoming X-radiation, behind the exposure position and behind a ray-protective screen which is located intermediate the exposure position and the supply magazine, and in which the conveying means for the film sheets, leading into the exposure position and leading from the exposure position, are continually conveyed in the region of the ray-protective screen. In this manner, there is achieved that the width of the X-ray examining apparatus may be reduced down to the width of the exposure installation. This will result in shorter exposure sequences when the conveying means for the film sheets are also located within the region of the ray-protective screen, since the successive film exposure may again be shot while the previous film sheet still is located on the conveying means leading to the automatic developing arrangement.

In a preferred aspect of the invention, the conveyance of the unexposed film sheets may be effected from below upwardly into the exposure position, and the exposed film plates from above out of the exposure position. This manner of conveyance without reversing direction permits for the closest possible succession of film sheets, and thereby also the maintenance of the shortest possible film exposure intervals.

A particularly space-saving or compact construction of the X-ray examining apparatus may be achieved when, in accordance with the embodiment of the invention, the plane of the film sheets in the supply magazine is oriented so as to be approximately in parallel with the plane of the film sheets in the exposure position. Thereby achieved is a low depth for the X-ray examining apparatus.

The difference in height between the stationary automatic developing arrangement and the vertically adjustable exposure installation may be bridged in a simple manner when the conveying means for the exposed film sheets, in a further aspect of the invention, has associated therewith a light-sealed closeable drop chute having a lower inclined slide surface which leads to the automatic developing arrangement. The exposed film sheets then always land, irrespective of their inlet height, on the inclined slide surface leading toward the automatic developing arrangement.

A film protective conveyance in the zone of the drop chute is attained when the film sheets, in a further aspect of the invention, are approximately horizontally introduced into the drop chute. The thus introduced film sheets, due to their air resistance, then float downwardly in the drop chute for a predetermined distance in an almost horizontal position before their dropping velocities increase at an increasingly inclined position.

The foregoing allows for stabilization of the film sheets in their floating position within the drop chute when, in a further aspect of the present invention, the drop chute is provided at mutually opposite sides thereof with essentially horizontal film supports which project into the drop chute. These film supports prevent the film sheets from assuming a more inclined position with respect to the horizontal, in that the respective lower edge of the film sheets first contact one such film support and are thereby braked during their fall. In this manner, also in very high drop chutes, there is obtained slow downward floating of the inserted film sheets.

In accordance with the present invention, the X-ray examining apparatus is aimed at the examination of standing patients, in which a rack mounts the exposure insulation for vertical adjustment thereof. A supply of film sheets is provided with first conveying means which conveys unexposed film sheets from a magazine into an exposure position in the exposure installation. A second conveying means is provided for conveying the exposed film sheets from the exposure position into an automatic developing arrangement. X-ray protective screen means is positioned rearwardly of the exposure position, and the supply magazine for unexposed film sheets is located in the direction of the incoming X-radiation, rearwardly of the exposure position and of the X-ray protective screen for reducing the width of the exposure installation to a maximum of twice the width of the maximum exposure format and to a maximum width of 80 centimeters. The first and second conveyors are conducted through the region of the X-ray protective screen, with the first conveyor conveying the unexposed film from below upwardly into the exposure position, and the second conveyor conveying the exposed film sheet from upwardly out of the exposure position.

BRIEF DESCRIPTION OF THE DRAWINGS

Further details of the invention may now be ascertained in connection with a preferred embodiment thereof, taken in conjunction with the accompanying drawings; in which.

DETAILED DESCRIPTION

Figure 1:
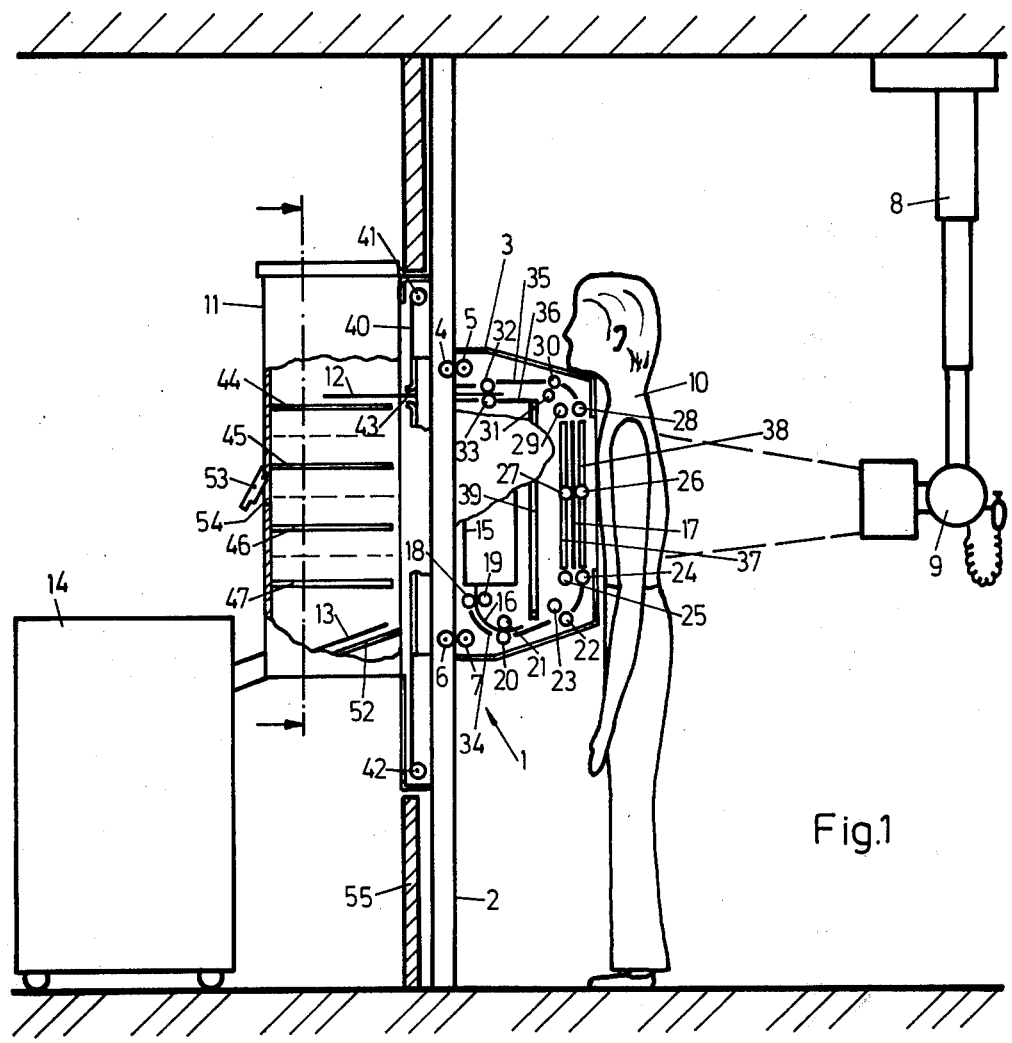
FIG. 1, in a partly sectional view, illustrates an X-ray examining apparatus utilized for the examination of standing patients, pursuant to the invention.
Figure 2:
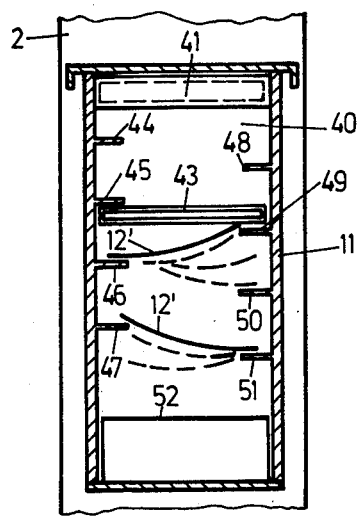
FIG. 2 is a sectional view taken along line II-II in FIG. 1.

In FIGS. 1 and 2 of the drawing the construction of an X-ray examining apparatus 1 is illustrated in side elevational views. On perpendicularly positioned U-rails 2 (only one shown in side view) there is supported in a vertically adjustable relationship an exposure installation 3, by means of rollers 4, 5, 6 and 7. A ceiling support 8, which may be a telescoping member, has an X-ray tube 9 suspended therefrom, the latter of which is operatively directed towards the exposure installation 3. A patient 10 is shown between the X-ray tube and the exposure installation, standing at the exposure installation. At the side of the exposure installation 3 which is directed away from the X-ray tube 9 there is located a drop chute 11 for receiving the exposed film sheets 12, 13, and which, in turn, has an automatic developing arrangement 14 communicating therewith. Through the partly sectionally illustrated ray-protectively constructed casing of the exposure installation 3, there may be ascertained a supply magazine 15 for the unexposed film sheets 16, 17, as well as conveying rollers 18 through 33, and guide plates 34, 35, 36, through the intermediary of which the unexposed film sheets 16, 17 are conveyed into a film exposure position between two intensifying foils 37, 38, and the exposed film sheets 12, 13 are conveyed from the exposure position into the drop chute 11. The intensifying foils 37, 38, which are located on both sides of the exposure position may, in a not detailed manner, be pressed against the particular film sheet 17 which is located in the exposure position during exposure thereof. Between the intensifying foils which encompass the exposure position of the film sheet and the supply magazine there is built-in a lead plate 39 forming a ray-protective screen in the exposure installation 3. The side of the drop chute 11 which is located adjacent the exposure installation 3 is open, and is only closed off by a light-sealingly closeable shade 40, which is wound along the surface and bottom of the drop chute 11 through the action of a spring-loaded roller 41, 42. The shade 40 is provided with a film inlet slit 43 which encompasses the two guide plates 35, 37 between which the film sheets egress from the vertically adjustable exposure installation 3 into the drop chute 11. Interiorly of the drop chute, as may be particularly ascertained from FIG. 2 of the drawing, at two oppositely located walls there are mounted horizontal film supports 44, 45, 46, 47, 48, 49, 50, 51; projecting inwardly into the space of the drop chute, and on the floor of the drop chute 11 an inclined positioned guide surface 52 along which the impinging film sheets glide into the automatic developing arrangement 14. The film supports preferably may project inwardly for about 5 to 20% of the width of the film sheets. One of the side walls of the drop chute has a slit 54 provided therein, which may be closed in a light-tight manner by means of a shutter 53 for the insertion of suitable, otherwise exposed film sheets.

At the commencement of the examination, the exposure installation is displaced along U-rails 2 to an elevation in conformance with the height of the respective patient 10. Through a generally known follower control (not shown), the length of the ceiling support or telescoping member 8, and consequently the elevation of the X-ray tube 9, is automatically coordinated with the vertical location of the exposure installation 3. Upon actuation of a sequencing or control key, the particular film sheet 36 located at that instance in the exposure position is, in a known manner, compressed between the intensifying foils 37, 38, and after compression is attained, the X-ray tube 9 is activated. Subsequently, the exposed film sheet is conveyed by conveying rollers 26 through 33 from the exposure position into the drop chute 11, while a new film sheet 16 is concurrently conveyed from the supply magazine 15 by means of conveying rollers 18 through 27 into the exposure position between the intensifying foils 37, 38. In the drop chute 11, the inserted film sheet 12 impinges with its leading edge against the chute wall which is opposite to the exposure installation and then floats slowly downwardly due to the high air resistance formed by its horizontal orientation. In view of the film supports 44 through 51 which are mounted on the opposite sidewalls so as to horizontally project into the interior of the chute, the film sheet, as shown in FIG. 2, is prevented from vertically dropping down in the drop chute 11, since the respective lowermost side edge of the film sheet is delayed during its fall by the successively lower film support. When the sheet is received by the lower inclined glide surface 52 of the drop chute 11, the film sheet then slides into the automatic developing arrangement 14 in which it is engaged by conveying means of the automatic developing arrangement and further transported.

Through the slit 54 in the slide wall of drop chute 11, which is in a light-tight closeable shutter 53 there may be inserted otherwise exposed film sheets. In this manner, the automatic developing arrangement 14 may be utilized to a much better extent, and in particular employed independently of the remaining X-ray examining apparatus. If, in the plane of the shade 40, there is provided a light-tight wall 55 which separates the room in which the X-ray examining apparatus is located into two halves, then the portion of the room in which the automatic developing arrangement 14 is located, independently of the portion of the room in which the exposure installation 3 of the X-ray examining apparatus is located, may be darkened for insertion of film sheets into the drop chute 11. In this instance, the examination of the respective patient 10 need not be interrupted when otherwise exposed film sheets are to be conveyed into the automatic developing arrangement. It is also possible that the lower inclined glide surface 52 in the drop chute 11 be rotated 90° about a vertical axis with respect to illustration of FIGS. 1 and 2, and to locate the automatic developing arrangement sideways of the drop chute. In this manner, there may be obtained a flexible coordination between the X-ray examining apparatus and the particular spatial relationships. It is also possible to connect a number of X-ray examining apparatus to various sides of the same drop chute.

It is essential to note, furthermore, that X-ray film sheets, particularly the two-sided emulsion layers on the film carrier foil, have such a high electrical resistance that electrical charges must be expected during all transport processes. However, electrostatic charges lead within the emulsion layer during charge equalization (small spark-overs) to transformations or changes in the emulsion layer which upon film processing appear in small sharp lines. These impede the diagnosis by the physician. However, the amount of electrostatic charge grows more than proportionally with the speed at which a surface, in this case the emulsion layer, slides along another object. One avoids, as best as one can, the transportation of unpacked film sheets in the direction where they are exposed, at an excessive speed. This effect restricts or limits the maximum exposure sequence frequencies obtainable with X-ray diagnostic equipment. The drop chute of the present invention, in which the film sheets, due to their high air resistance in the horiziontal position, drops at a relatively slow speed and thus avoids high speeds.

The film supports 44 through 51 which project into the drop chute, are provided with the express purpose of preventing the film sheets from dropping or falling with the front side forward in the vertical position.

Whereas the film sheets experience friction at the film supports 44 through 51, this relatively slow contact (dropping time up to approximately 4 seconds) of these film supports cannot be compared with the powerful impact of the film sheets in the case of the prior art.

While there has been shown what is considered to be the preferred embodiment of the invention, it will be obvious that modifications may be made which come within the scope of the disclosure of the specification.

What is claimed is:

1. In an X-ray examining apparatus for the examination of standing patients, including support means supporting an X-ray tube; an exposure installation; a rack mounting said exposure installation for vertical adjustment thereof; a supply magazine for film sheets having first conveying means for conveying unexposed film sheets from said magazine into an exposure position in said exposure installation; and second conveying means for conveying exposed film sheets from said exposure position into an automatic developing arrangement, the improvement comprising X-ray protective screen means positioned rearwardly of said exposure position, said supply magazine for unexposed film sheets being located, in the direction of the incoming X-radiation, rearwardly of said exposure position and of said X-ray protective screen means for reducing the width of the exposure installation to a maximum of twice the width of the maximum exposure format and to a maximum width of 80 centimeters, said first and second conveying means for conveying unexposed film sheets into the exposure position and exposed film sheets from said exposure position being conducted through the region of said X-ray protective screen means, said first conveying means conveying said unexposed film sheets from below upwardly into the exposure position, and said second conveying means conveying said exposed film sheets from upwardly out of the exposure position.

2. An apparatus as claimed in claim 1, comprising a light-tight closeable drop chute communicating with said second conveying means for receiving exposed film sheets therefrom, and a downwardly inclined glide surface being provided in the lower portion of said drop chute for conveying said exposure film sheets towards sais automatic developing arrangement, said drop chute including means for horizontal insertion thereinto of said exposed film sheets; and a plurality of substantially horizontal film supports in said drop chute projecting into said drop chute from opposite inner side walls thereof, said film supports being located in interstitial relationship and projecting into said drop chute for about 5 to 20% of the width of the film sheets.

3. An apparatus as claimed in claim 1, the film sheets in said supply magazine being oriented in a plane extending approximately parallel with the plane of the film sheets in the exposure position.

4. An apparatus as claimed in claim 2, comprising a film inlet slit being formed in the wall of said drop chute adjacent said exposure installation; and shade means being fastened to the upper and lower ends of said drop chute adapted to close said slit in a light-tight manner, said shade having a film sheet inlet slit being connected to guide plates of said exposure installation.

5. An apparatus as claimed in claim 2, at least one further light-tight closeable film sheet inlet slit being formed in the side wall of said drop chute.

6. An apparatus as claimed in claim 1, comprising a light-tight separating wall for separating a portion of the room containing the automatic developing arrangement and said drop chute from a portion of the room containing said exposure installation and said X-ray tube.

7. In an X-ray examining apparatus for the examination of standing patients, including support means supporting an X-ray tube; an exposure installation; a rack mounting said exposure installation for vertical adjustment thereof; a supply magazine for film sheets having first conveying means for conveying unexposed film sheets from said magazine into an exposure position in said exposure installation; and second conveying means for conveying exposed film sheets from said exposure position into an automatic developing arrangement, the improvement comprising X-ray protective screen means positioned rearwardly of said exposure position, said supply magazine for unexposed film sheets being located, in the direction of the incoming X-radiation, rearwardly of said exposure position and of said X-ray protective screen means, said first and second conveying means for conveying unexposed film sheets into the exposure position and exposed film sheets from said exposure position being conducted through the region of said X-ray protective screen means, said first conveying means conveying said unexposed film sheets from below upwardly into the exposure position, and said second conveying means conveying said exposed film sheets from upwardly out of the exposure position; a light-tight closeable drop chute communicating with said second conveying means for receiving exposed film sheets therefrom, and a downwardly inclined glide surface being provided in the lower portion of said drop chute for conveying said exposed film sheets towards said automatic developing arrangement, said drop chute including means for horizontal insertion thereinto of said exposed film sheets; and a plurality of substantially horizontal film supports in said drop chute projecting into said drop chute from opposite inner side walls thereof, said film supports being located in interstitial relationship and projecting into said drop chute for about 5 to 20 percent of the width of the film sheets.

* * * * *